United States Patent
Bronner et al.

(10) Patent No.: US 10,188,813 B2
(45) Date of Patent: Jan. 29, 2019

(54) DEVICE AND METHOD FOR ARTIFICIAL RESPIRATION IN EMERGENCIES

(71) Applicant: Karl Kuefner GmbH & Co. KG, Albstadt-Truchtelfingen (DE)

(72) Inventors: Rolf Bronner, Baden-Baden (DE); Joachim Hiller, Goeppingen (DE); Till Kaz, Stuttgart (DE)

(73) Assignee: Karl Kuefner GmbH & Co. KG, Albstadt-Truchtelfingen (DE)

( * ) Notice: Subject to any disclaimer, the term of this patent is extended or adjusted under 35 U.S.C. 154(b) by 313 days.

(21) Appl. No.: 14/786,705

(22) PCT Filed: May 13, 2014

(86) PCT No.: PCT/DE2014/100166
§ 371 (c)(1),
(2) Date: Oct. 23, 2015

(87) PCT Pub. No.: WO2014/183747
PCT Pub. Date: Nov. 20, 2014

(65) Prior Publication Data
US 2016/0074604 A1 Mar. 17, 2016

(30) Foreign Application Priority Data

May 13, 2013 (DE) .......................... 10 2013 208 776
Nov. 13, 2013 (DE) .......................... 10 2013 223 125

(51) Int. Cl.
*A61M 16/00* (2006.01)
*A61M 16/06* (2006.01)
*A61M 16/10* (2006.01)

(52) U.S. Cl.
CPC .... *A61M 16/0048* (2013.01); *A61M 16/0003* (2014.02); *A61M 16/0051* (2013.01);
(Continued)

(58) Field of Classification Search
None
See application file for complete search history.

(56) References Cited

U.S. PATENT DOCUMENTS

| | | | |
|---|---|---|---|
| 4,520,811 A | 6/1985 | White et al. | |
| 6,155,257 A | 12/2000 | Lurie et al. | |

(Continued)

FOREIGN PATENT DOCUMENTS

| | | |
|---|---|---|
| DE | 24 02 192 A1 | 7/1975 |
| DE | 10 2007 061 842 A1 | 6/2008 |

(Continued)

OTHER PUBLICATIONS

International Search Report of PCT/DE2014/100166, dated Sep. 16, 2014.

(Continued)

*Primary Examiner* — Michael R Bloch
(74) *Attorney, Agent, or Firm* — Collard & Roe, P.C.

(57) ABSTRACT

A device and a method for artificial respiration in emergencies are proposed. The device comprises respiratory mask (40) which can be placed onto the nose and mouth section of a person to be provided with artificial respiration, a mouth section mouthpiece (41), through which respiratory air from an aider can be supplied, a flow tube (2) disposed between the respiratory mask (40) and the mouthpiece (41), which flow tube forms a continuous flow channel for the supplied respiratory air from the mouthpiece (41) to the respiratory mask (40), at least one sensor (10) disposed in the flow channel of the flow tube (2), which sensor measures parameters of the gases flowing through the flow channel, a processor disposed on the flow tube (2) and an output device (124). Here, the processor processes the mass or volumetric flow registered by the flow sensor (19) to form an output signal. The output device (124) emits the output signal.

18 Claims, 15 Drawing Sheets

Figure 1:
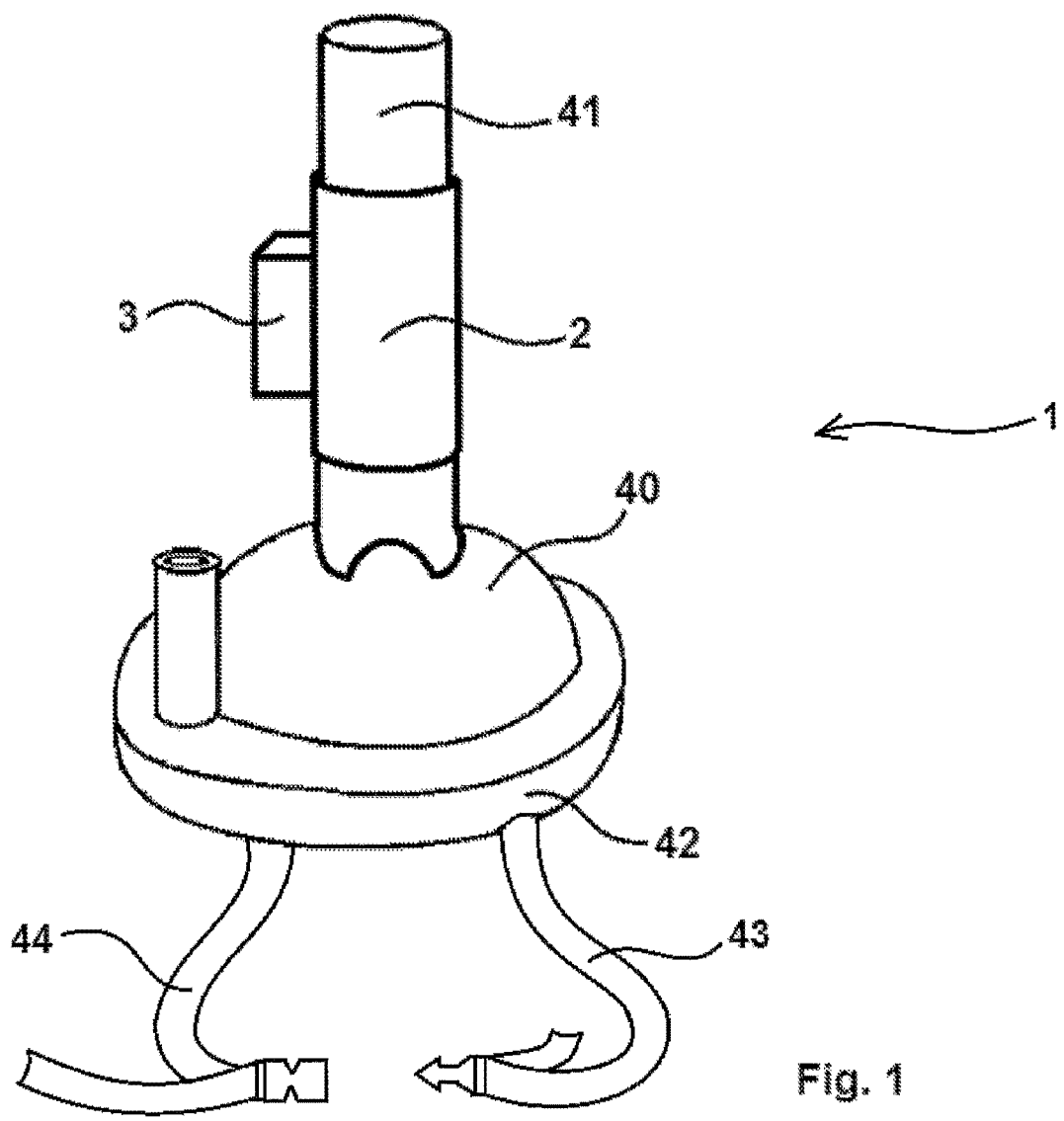

(52) U.S. Cl.
CPC .......... *A61M 16/021* (2017.08); *A61M 16/06* (2013.01); *A61M 16/105* (2013.01); *A61M 16/106* (2014.02); *A61M 2016/003* (2013.01); *A61M 2205/3334* (2013.01); *A61M 2205/3546* (2013.01); *A61M 2205/502* (2013.01); *A61M 2205/75* (2013.01)

(56) References Cited

U.S. PATENT DOCUMENTS

| | | | |
|---|---|---|---|
| 7,004,168 B2 | 2/2006 | Mace et al. | |
| 7,774,060 B2 | 8/2010 | Westenskow et al. | |
| 2001/0031224 A1 | 10/2001 | Labuda et al. | |
| 2003/0192547 A1* | 10/2003 | Lurie | A61H 31/005 128/207.12 |
| 2004/0082888 A1* | 4/2004 | Palazzolo | A61B 5/04012 601/41 |
| 2004/0230140 A1 | 11/2004 | Steen | |
| 2005/0085799 A1 | 4/2005 | Luria et al. | |
| 2006/0270952 A1* | 11/2006 | Freeman | A61H 31/005 601/41 |
| 2009/0171257 A1* | 7/2009 | Centen | A61F 5/0118 602/21 |
| 2010/0036266 A1* | 2/2010 | Myklebust | A61B 5/02444 600/500 |
| 2010/0106040 A1 | 4/2010 | Orr et al. | |
| 2010/0256539 A1* | 10/2010 | Strand | A61H 31/005 601/41 |
| 2010/0319691 A1 | 12/2010 | Lurie et al. | |
| 2011/0034836 A1 | 2/2011 | Halperin et al. | |
| 2011/0040217 A1* | 2/2011 | Centen | A61B 5/0064 601/41 |
| 2011/0112423 A1* | 5/2011 | Chapman | A61B 5/02 600/528 |
| 2011/0284004 A1* | 11/2011 | Silver | A61B 5/087 128/205.13 |
| 2012/0302910 A1* | 11/2012 | Freeman | A61M 16/00 600/538 |
| 2014/0275820 A1* | 9/2014 | Varga | A61M 16/0078 600/301 |
| 2015/0238722 A1 | 8/2015 | Al-Ali | |

FOREIGN PATENT DOCUMENTS

| | | |
|---|---|---|
| EP | 1 858 472 A1 | 8/2013 |
| GB | 2 379 612 A | 3/2003 |
| WO | 01/15761 A1 | 3/2001 |

OTHER PUBLICATIONS

German Search Report in 10 2013 208 776.4, dated Dec. 18, 2013, with an English translation of relevant parts.
German Search Report dated Mar. 3, 2015 in German Application No. 10 2014 209 053.9 with English translation of relevant parts.
European Search Report in EP 15 167 490.0, dated Sep. 18, 2015, with English translation.

* cited by examiner

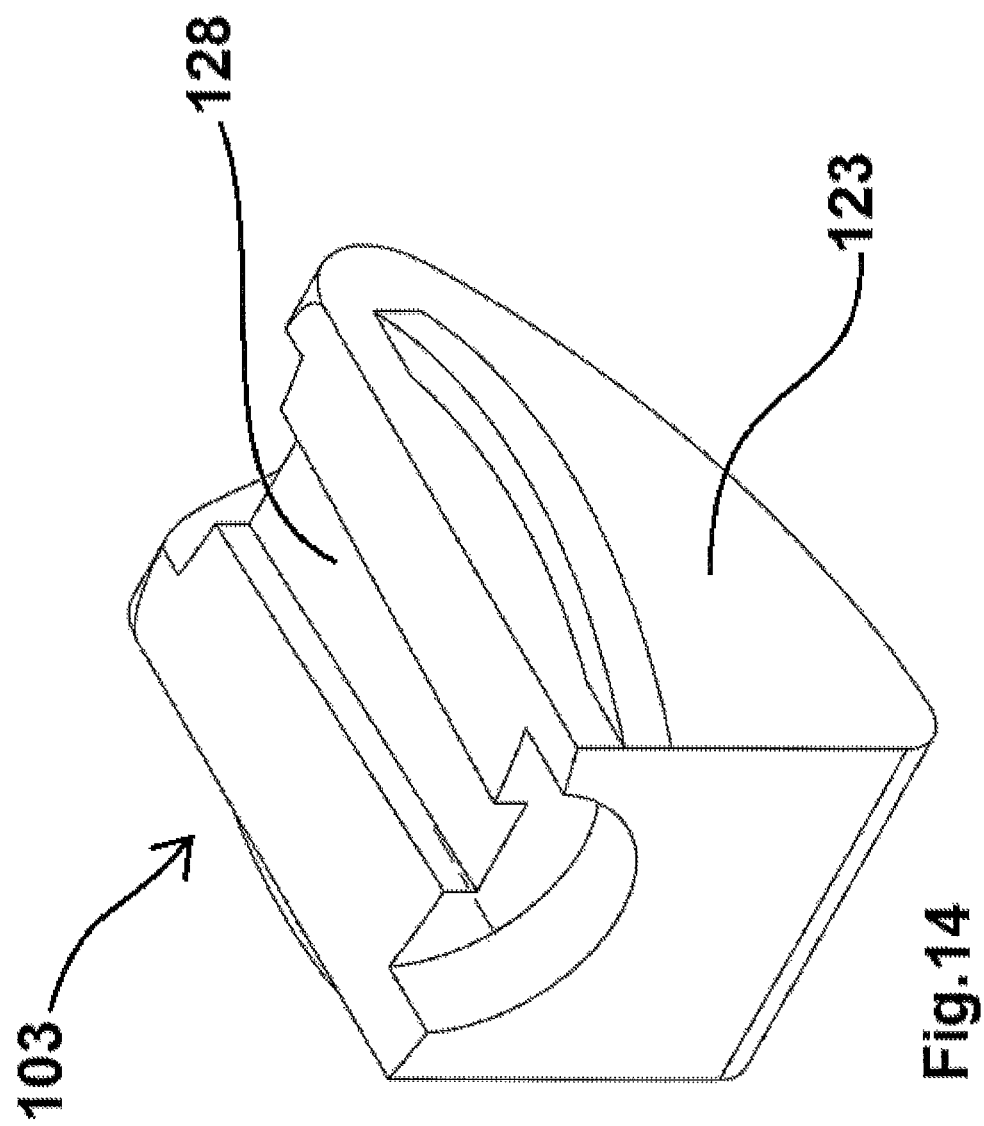

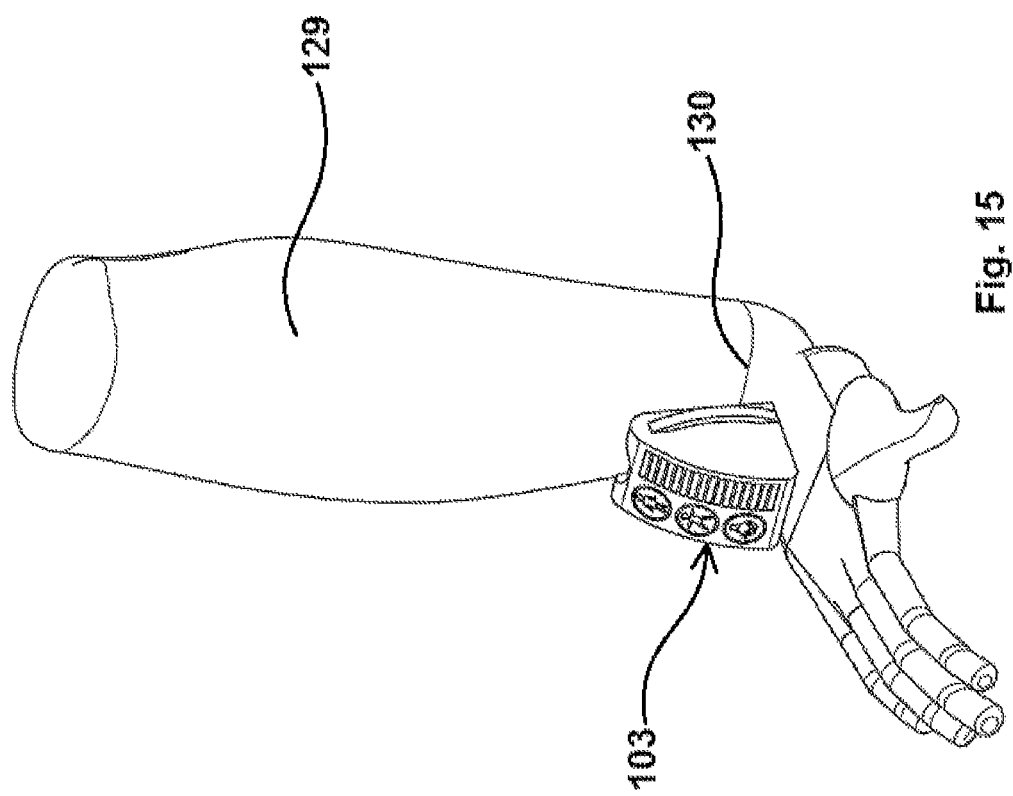

DEVICE AND METHOD FOR ARTIFICIAL RESPIRATION IN EMERGENCIES

CROSS REFERENCE TO RELATED APPLICATIONS

This application is the National Stage of PCT/DE2014/100166 filed on May 13, 2014, which claims priority under 35 U.S.C. § 119 of German Application Nos. 10 2013 208 776.4 filed on May 13, 2013 and 10 2013 223 125.3 filed on Nov. 13, 2013, the disclosures of which are incorporated by reference. The international application under PCT article 21(2) was not published in English.

The invention derives from a device and a method for artificial respiration in emergencies.

In an accident or other medical emergency, the affected persons need to be given first aid by first responders until professional rescue services arrive. First responders are individuals who, by chance, are in a position to take life-saving emergency action in an accident or medical emergency. If the person who has suffered an accident or a medical emergency has entirely or partially ceased to breathe independently or has suffered a circulatory arrest, measures to resuscitate them and to overcome the respiratory arrest must be taken. These include cardiopulmonary resuscitation. If the airways are blocked or obstructed, the airways of the affected person must first be cleared. It may be necessary for an aider to give the person respiration. In a circulatory arrest a cardiac massage must be performed. The purpose of this measure is to supply the vital organs of the affected person with oxygen.

In the following, the person who is receiving emergency medical attention is described as the person. The person who is providing first aid is described as the aider in the following. In the following, resuscitation measures are those that are suitable for maintaining a circulation to a certain extent in order to supply the most important organs until professional rescue services arrive.

The simplest form of respiration is artificial respiration by mouth-to-mouth resuscitation. Here, with the head of the casualty or person in an emergency situation extended, their nose is sealed and air is insufflated through the mouth.

Excessive pressure must be avoided in this process to prevent aspiration, namely the penetration of saliva, fluid or other matter into the respiratory passages. An adequate volume is achieved when rising of the thorax of the casualty or person in an emergency situation can be identified.

Potential first responders often have no or inadequate knowledge of first aid. For fear of making mistakes due to this inadequate knowledge, often no or inadequate first aid is provided. In addition, potential first responders often do not recognize a respiratory arrest or a circulatory arrest. The necessary assistance is consequently not given. In mouth-to-mouth resuscitation the aider comes into direct contact with bodily fluids of the casualty or person in an emergency situation, creating the possibility of disease transmission. Inhibitions therefore often arise.

Known respiration aids such as masks or films that can be placed on the mouth and nose of a casualty or person in an emergency situation avoid direct contact between the casualty or person in an emergency situation on the one hand and the aider on the other. This reduces the risk of infection. Known respiration aids are equipped with a mouthpiece via which the aider blows in their own respiratory air. The exhaled air of the casualty or person in an emergency situation escapes through the mask after artificial respiration and does not return to the aider. Problems in the use of known respiration aids are the occurrence of leakage, increased respiration resistance and possibly the aider's limited knowledge of the respiration time and the required quantity of inhaled air. The problems of the aider's limited knowledge of how to administer cardiac massage also apply to the use of known respiration aids.

The invention is based on the task of providing a .device and a method for artificial respiration in emergencies, where an aider can supply respiratory air to a casualty or person in an emergency situation without making direct bodily contact with their nose and mouth, and where the aider is assisted with supplying respiratory air and administering cardiac massage even if they have no or limited knowledge of first aid.

This task is solved by a device with the characteristics according to one aspect of the invention and by a method with the characteristics according to another aspect of the invention. The device according to the invention is characterized in that there is a flow tube disposed between a respiratory mask which can be placed onto the nose and mouth of a casualty or person in an emergency situation on the one hand and a mouthpiece for the aider on the other hand. This constitutes a continuous flow channel for the air supplied or flowing away from to the person. There is a flow sensor that protrudes into the flow channel disposed on the flow tube. The air led through the flow channel passes around the flow sensor, which registers the mass or volumetric flow of a gas flowing through the flow channel. The volumetric flow of a gas flowing through the flow tube here corresponds to a volume that passes through a specified cross-section of the flow tube per unit of time. The mass flow or mass flow rate of a gas flowing through the flow tube corresponds to a mass that passes through a specified cross-section of the flow tube per unit of time.

The volumetric flow or flow rate of the respiratory air supplied to the person is also referred to as the inspiratory flow. The volumetric flow or flow rate of the air flowing out of the person is also referred to as the expiratory flow.

A rate of change in the mass or volumetric flow can also be determined from the mass or volumetric flow.

The respiratory mask rests on the person's face. If required it may be secured to the person's head with a strap or belt to keep it in position. Thanks to its soft, elastic edge, the respiratory mask lies basically airtight on the person's face. This results in most of the air flowing out of the person's nose or mouth reaching the flow tube and flowing through it. In doing so, it passes the flow sensor, so that the mass or volumetric flow of the flowing air is determined. In addition, the air supplied via the mouthpiece by an aider passes through the flow tube into the respiratory mask, and from there into the person's nose and/or mouth. The mass or volumetric flow of the supplied air is likewise registered when it flows through the flow tube. It can be ascertained from the timing of an output signal emitted on the output device whether the output refers to a mass or volumetric flow of an air supplied by the aider or to an air flowing out of the person. If an output signal is emitted by the output device concurrently with the supply of air, it refers to the supplied air. On the other hand, if an output signal is emitted without air being supplied by the aider or if it is emitted at a different time to the supply of air, the output signal refers to an air flowing out of the person.

By means of the device it can be registered whether the casualty or person in an emergency situation has entirely or partially ceased to breathe before artificial respiration or a cardiac massage is performed. If the person has ceased to breathe, the flow sensor will indicate no mass or volumetric flow. There will then be no corresponding output signal. On the other hand if a mass or volumetric flow is determined, this is a sign that the person is breathing spontaneously. Furthermore, it can be established whether the respiratory air supplied by the aider is sufficient to terminate the respiratory arrest.

If cardiac massage is administered, the thorax of the person is compressed by applying pressure. After the pressure is released, decompression takes place. The thorax expands again. This process is constantly repeated. When the thorax is compressed, the person's heart and lungs in particular are compressed. To a limited extent this supports a circulation of the blood to vital organs, in particular the person's brain. Compression of the lungs results in air flowing out of the nose or mouth of the person, provided the person's airways are not obstructed. If no mass or volumetric flow from the person is indicated in a cardiac massage during compression of the person's thorax, this is therefore a sign that the person's airways are obstructed. This applies in particular if no mass or volumetric flow is registered despite an increase in penetration depth in the cardiac massage. The airways may be obstructed by the person's tongue or by vomit.

If the airways are clear, it can be ascertained from the mass or volumetric flow registered by the flow sensor whether the penetration depth in the cardiac massage is sufficient to maintain an essential circulation for resuscitation and to supply certain organs. Certain ranges are specified here. The penetration depth corresponds to the distance by which the thorax is pressed in during compression. The mass or volumetric flow shown during compression of the thorax is relative to the penetration depth of the thorax.

It can also be established whether the person's airways are obstructed as the aider insufflates air via the mouthpiece of the device and the flow sensor determines the mass or volumetric flow. The mass or volumetric flow in the flow tube depends on whether the airways are clear or obstructed and whether the oesophagus of the person is possibly also blocked. If the person's airways are clear, air supplied by the aider passes into the lungs of the person. If the person's airways are obstructed and the oesophagus is blocked, air supplied by the aider passes into the stomach of the person. If the person's airways and oesophagus are blocked, air supplied by the aider passes only into the mouth of the person. The three scenarios stated indicate a typical pattern to the mass or volumetric flow, which may be stored in the apparatus as a characteristic. By comparing the progress in time of the mass or volumetric flow with these characteristics, it can be established whether the airways are obstructed even if no cardiac massage is administered. Artificial respiration involving supplying air via the mouthpiece is sufficient to achieve this.

The device is equipped with a processor and an output device. The mass or volumetric flow registered by the flow sensor is processed in the processor. The signals of the flow sensor are processed to that end. An output signal that is emitted by the output device is generated.

An aider thus receives assistance in administering first aid. The first aid can be adapted optimally to the needs of the person. In this way, inhibitions in potential aiders can be overcome.

The determination of the parameters for the gases flowing in the flow tube also continues during first aid. As a result, the instructions given to the aider during the course of first aid can be adapted continually to any changes in the condition of the person in an emergency situation.

The device is equipped preferably with an energy storage device, for example a battery.

It is beneficial that the device features a storage device. Data, signals and/or measured values for the mass or volumetric flow registered or parameters derived therefrom are stored in the storage device. Characteristics relating to the typical progress in time for the supply of air, if the airways are clear or obstructed and possibly also the oesophagus blocked, can be stored in the storage device. In addition, different ranges for a sufficient mass or volumetric flow for resuscitation can be stored in the storage device for different groups of persons, for example adults, children and infants. In addition to the possible measured values or measured-value ranges, recommendations for the aider on how to proceed can be stored in the storage device. In this case the processor matches up the measured values registered by the sensor with appropriate instructions or recommendations stored in the memory. These are emitted to the aider by means of an output device. In this way, the aider can be informed continuously of what steps they should take, adapting the steps to the prevailing condition of the casualty or person in an emergency situation. The aider is for example informed when they should supply respiratory air to the casualty or person in an emergency situation, when they should start to administer cardiac massage, how often and at what time intervals they should exert pressure to the thorax of the casualty or person in an emergency situation before supplying respiratory air again.

According to an advantageous embodiment of the invention, at least one further sensor is provided on the flow tube to determine parameters of the airflow and/or of the gases contained in the flowing air. The parameters represent in particular physical or chemical properties of the gases. These include for example:

airway pressure relative to the surroundings,
ambient pressure,
pressure difference,
temperature,
humidity,
oxygen content or oxygen concentration,
carbon dioxide content or carbon dioxide concentration.

The sensor or sensors are designed to determine the above parameters. The parameters such as respiratory flow, pressure difference, oxygen or carbon dioxide concentration are also referred to as vital signs of the person. Sensors that determine the above parameters are therefore also referred to as vital signs sensors.

According to an advantageous embodiment of the invention, in addition to the flow sensor the device is equipped with a vital signs sensor by means of which a proportion of oxygen and carbon dioxide in the air flowing through the flow channel can be determined. The processor is designed such that it processes the registered proportion of oxygen and carbon dioxide to produce an output signal that is emitted by the output device.

Oxygen is converted into carbon dioxide in the person's lungs. This conversion also occurs during respiration or a cardiac massage if the person is not breathing independently and has suffered circulatory arrest. Therefore, if the sensor demonstrates that the carbon dioxide concentration in the air flowing out of the person is greater than the air supplied to the person, this is an indication that the air supplied by artificial respiration or cardiac massage has reached the person's lungs. A corresponding confirmation of a carbon dioxide content or a carbon dioxide concentration can therefore also provide information about artificial respiration or cardiac massage, and in particular about whether the measure in question meets the requirement for resuscitation.

According to an advantageous embodiment of the invention, the penetration depth in a cardiac massage is determined by means of the proportion of oxygen and carbon dioxide registered. This depends on the proportion of oxygen and carbon dioxide registered.

According to an advantageous embodiment of the invention, the output device is an optical display device. The optical display device exhibits for example a screen or a monitor.

According to a further advantageous embodiment of the invention, the optical display device exhibits a combination of several light sources. Suitable light sources include light-emitting diodes in different colors, for example. The different colors can represent different ranges of the mass or volumetric flow for the person measured with the flow sensor or a parameter derived therefrom. For example, a first color can represent a mass or volumetric flow that is less than or equal to a specified minimum. A second color can represent a mass or volumetric flow that is greater than or equal to a specified maximum. A third color can represent a mass or volumetric flow that is between the minimum and the maximum. Different minimum and maximum values can be specified here for different groups of people, for example adults, children and infants. These are preferably stored in a memory device in the device. In this case the device is preferably equipped with an input device for selection of the group of people to which the person in an emergency belongs.

According to a further advantageous embodiment of the invention, the optical display device exhibits an optically active surface on which the output signal is displayed. It is beneficial that this optically active surface is convex.

Alternatively, the surface can also take the form of an essentially flat surface. It is beneficial that the flat optically active surface is aligned at an angle of more than 0° and less than 90° to the longitudinal direction of the flow tube. The longitudinal direction of the flow tube here corresponds essentially to the direction of flow of the gases flowing through the flow tube. The curvature of the optically active surface or the angle of the optically active surface to the flow tube makes it easier for the aider to identify the output signal displayed on the display device while the device is fitted to the person in an emergency situation.

According to a further advantageous embodiment of the invention, the output device exhibits an acoustic output device. In this case the output signal is emitted to the aider by a microphone, for example. The optical display device and acoustic output display device can also be combined with each other.

According to a further advantageous embodiment of the invention, the output device comprises an interface for the output of data concerning a mass or volumetric flow registered by the flow sensor, or data derived therefrom, to a mobile telecommunications device. It can also be an interface for data transmission by radio, such as Bluetooth, or an interface for data transmission over a data line. In this case the output signal can also be emitted via the mobile telecommunications device. In addition, the output signals can be stored in a memory device of the telecommunications device for retrieval at a later point in time.

Several different output devices can also be provided, so that the steps to be taken are emitted to the aider in various different ways.

According to a further advantageous embodiment, the device is equipped with an interface over which data concerning a mass or volumetric flow registered by the flow sensor or data derived therefrom can be emitted to an external device for emergency care, to a medical device or to a computer. The data can now be called up and is available for the subsequent care of the patient. A paramedic, a doctor or a nurse can now swiftly and easily form an impression of the condition of the person and of what first aid has already been administered. The medical device may for example be a respirator or a defibrillator.

According to a further advantageous embodiment of the invention, there is a first filter disposed in the flow channel between the mouthpiece and the flow sensor. The filter ensures that the air entering through the filter flows as evenly as possible around the flow sensor. The aim is to generate an ideally laminar flow. In addition, the filter prevents particles from reaching the flow tube and damaging the flow sensor. The first filter can for example consist of a plastic or metal lattice or mesh, in particular wire, of a nonwoven material or of a metal and/or plastic fabric.

According to a further advantageous embodiment of the invention, there is a second filter disposed in the flow channel between the respiratory mask and the flow sensor. In exactly the same way as the first filter, it promotes the flow of the air or the air mixture through the flow tube along the sensor, with the objective of generating an ideally laminar flow. Furthermore, the second filter prevents the penetration of particles into the flow tube that could damage the flow sensor. These include emissions by the person in a medical emergency situation. The second filter can for example consist of a plastic or metal lattice or mesh, in particular wire, of a nonwoven material or of a metal and/or plastic fabric.

According to a further advantageous embodiment of the invention, a third filter is arranged between the respiratory mask and the flow sensor to trap moisture in the air flowing out of the person, thus preventing the person's lungs from drying out excessively. This third filter can in addition trap emissions by the person. The third filter can for example consist of a plastic or metal lattice or mesh, in particular wire, of a nonwoven material or of a metal and/or plastic fabric.

According to a further advantageous embodiment of the invention, the cross-section of the end of the flow tube facing the mouthpiece is matched to known respirators and their accessories. Upon the arrival of professional rescue services, they can remove the mouthpiece from the flow tube and connect a respirator to the flow tube. The respiratory mask and the flow tube can remain on the patient.

According to a further advantageous embodiment of the invention, the processor takes the form of a processor generating the penetration depth signal. In a cardiac massage the thorax of the person in a medical emergency situation is compressed by a distance that is referred to as the penetration depth. During this compression of the thorax, air flows out of the nose and/or mouth of the person. It passes through the respiratory mask into the flow tube and there flows around the flow sensor, by means of which the mass or volumetric flow of the air flowing out of the person is determined. The mass or volumetric flow is relative to the penetration depth. The processor generates a characteristic penetration depth signal for the penetration depth from the registered mass or volumetric flow. The output device is designed to emit the penetration depth signal as an output signal. The penetration depth signal is therefore an output signal as indicated above. The aider thus receives information on whether the penetration depth down to which they have compressed the thorax of the person is sufficient to supply the person until professional rescue services arrive.

According to a further advantageous embodiment of the invention, a sensor fixture device is arranged on one wall of the flow tube. The sensor fixture device extends at least partly into the flow channel of the flow tube. The flow sensor is arranged on the section of the sensor fixture device that extends into the flow channel. In this way, the flow sensor is secured to the flow tube in such a way that it extends into the gas flowing in the flow tube and reliably determines the mass and volumetric flow.

According to a further advantageous embodiment of the invention, the device is equipped with a push-on part in which the processor and the output device are arranged. Optionally, a storage device and one or more interfaces, as appropriate, are additionally arranged in the push-on part. The push-on part is connected detachably to the flow tube. It can be separated from the flow tube without the push-on part or the flow tube becoming damaged or destroyed. The push-on part exhibits a housing in which the processor and the output device are arranged in a well-protected manner. Because the push-on part does not come into contact with the patient and the respiratory air, it can be reused. The flow tube, the mouthpiece and the respiratory mask can either be disposed of after use or cleaned, disinfected and reused.

According to a further advantageous embodiment of the invention, the push-on part encompasses the flow tube at least in part.

According to a further advantageous embodiment of the invention, the push-on part exhibits an arm fastening device with which it can be fastened to an arm of an aider. Furthermore, the push-on part is equipped with an acceleration sensor that determines acceleration of the arm during cardiac massage. If the flow sensor determines that the airways of the person are obstructed, and if it should not be possible to clear the airways, the aider can detach the push-on part from the flow tube and fasten it to his arm. For administering cardiac massage, the penetration depth is now determined from the acceleration with which the aider moves their arm during cardiac massage, instead of by registering the mass or volumetric flow. Changeover from the flow sensor to the acceleration sensor takes place preferably automatically when the push-on part is detached from the flow tube. Here, the flow sensor remains on the flow tube.

According to a further advantageous embodiment of the invention, the processor is designed such that it generates an output signal that can be emitted with the output device from the acceleration registered by the acceleration sensor.

According to a further advantageous embodiment of the invention, at least two grip recesses and/or outward-protruding handle elements are arranged on the push-on part.

According to a further advantageous embodiment of the invention, the device exhibits a vital signs sensor. This is used to determine the pressure difference in the flow channel and/or the oxygen concentration and/or the carbon dioxide concentration and/or other flow parameters as a person's vital signs, in addition to the mass or volumetric flow of the gases flowing through the flow channel.

According to a further advantageous embodiment of the invention the sensor takes the form of a respiration response sensor that determines the respiration response characteristic of the person, and the processor takes the form of a respiration response processor that evaluates the respiration characteristic and determines whether the airways of the person are obstructed. The result of the evaluation is emitted via the output device. In this way an aider obtains information on whether the airways of the person to be given respiration are obstructed or clear.

According to a further advantageous embodiment of the invention, the device exhibits an input device via which certain characteristics of the person in a medical emergency situation may be input. Thus, the aider can for example select at the input device whether the person is an adult, a child or an infant. The ranges specified for resuscitation differ between these groups of people, with the result that the aider can be informed accordingly.

The method according to the invention in a further embodiment is characterized in that with the help of the device after the respiratory mask has been fitted to a person in a medical emergency situation, the gases flowing out of the person that pass through the flow tube are registered by a flow sensor arranged in the flow tube. To that end the mass or volumetric flow of the gas flowing in the flow tube is registered. The mass or volumetric flow registered is processed into an output signal with the aid of the processor. The output signal is emitted by the output device.

The aider receives preferably not merely general advice on artificial respiration or the cardiac massage, but specific instructions that are adapted to the condition of the person in an emergency situation. Determination of the mass and volumetric flow and emission of the output signal continue while first aid is being administered. As a result, the instructions given to the aider during the course of first aid can be adapted continually to any changes in the condition of the person in an emergency situation.

According to a further advantageous embodiment of the invention, the gases flowing in the flow tube in both directions are registered by the flow sensor. This means that not only is the mass or volumetric flow in the air flowing out of the person registered, but also the air supplied to the patient.

According to a further advantageous embodiment of the method according to the invention, a mass or volumetric flow of the air flowing out of the nose and/or mouth of the person and through the flow tube during a cardiac massage as a result of compression of the thorax down to a penetration depth is registered by the flow sensor. A characteristic penetration depth signal is generated by the processor from the registered mass or volumetric flow. The penetration depth signal is emitted by the output device as the output signal.

According to a further advantageous embodiment of the method according to the invention, the output device indicates whether the mass or volumetric flow registered or the penetration depth signal derived from it or another parameter derived from the mass or volumetric flow lies within a specified range for resuscitation. The range is specified such that a circulation of the blood that provides a blood supply to the brain takes place within this range.

According to a further advantageous embodiment of the method according to the invention, before a cardiac massage starts the mass or volumetric flow of the air flowing out of the person's nose and/or mouth is registered by means of the flow sensor. Whether the mass or volumetric flow registered is within a specified range for spontaneous breathing is emitted by the output device. In this way it can be established whether the person is breathing independently.

According to a further advantageous embodiment of the invention, the acceleration with which the thorax is compressed is registered by means of an acceleration sensor during compression of the thorax. A characteristic penetration depth signal is generated from the acceleration determined. The penetration depth signal is emitted as an output signal by means of the output device. The output device indicates whether the acceleration registered or the penetration depth signal derived from it or another parameter derived from the acceleration lies within a specified range for resuscitation.

According to a further advantageous embodiment of the invention, the output signal is emitted not only to the aider, but also to third parties who are involved in the subsequent medical care of the person in an emergency situation. These parties will typically be medical specialists such as paramedics, nurses or doctors, rather than first responders.

Further advantages and advantageous embodiments of the invention can be obtained from the following description, the drawing and the claim.

DRAWING

Figure 5:
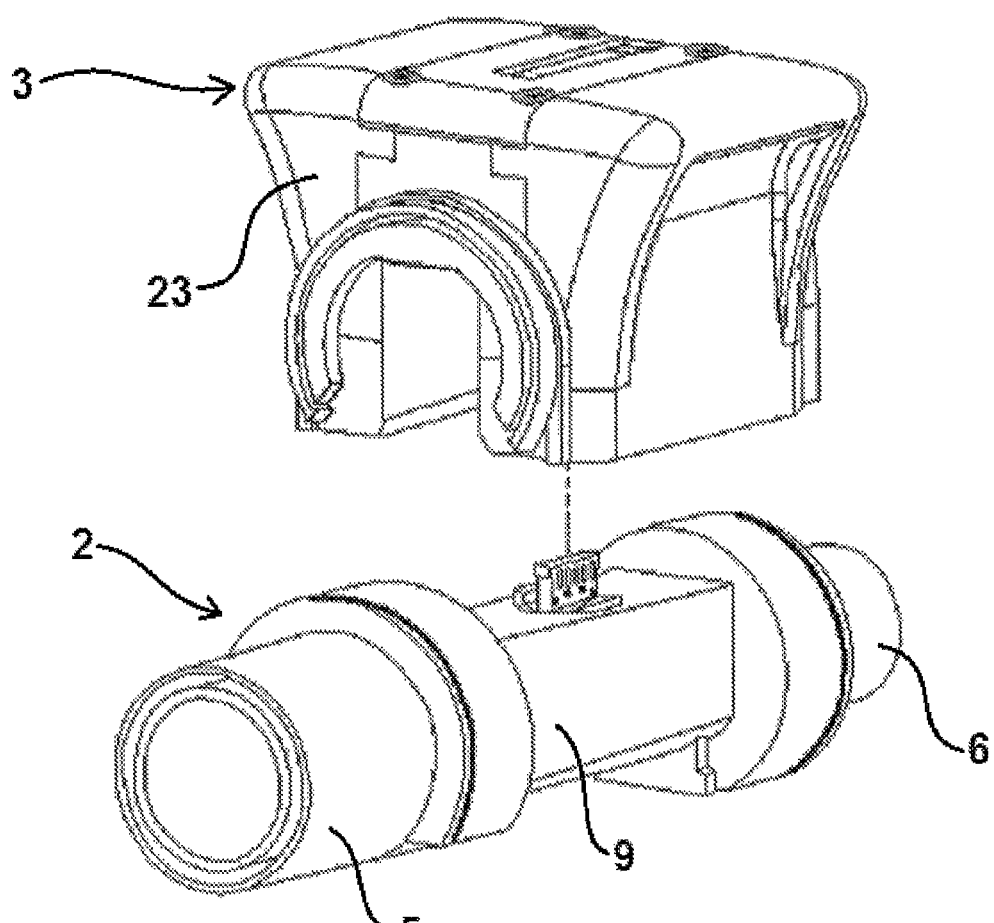
Figure 6:
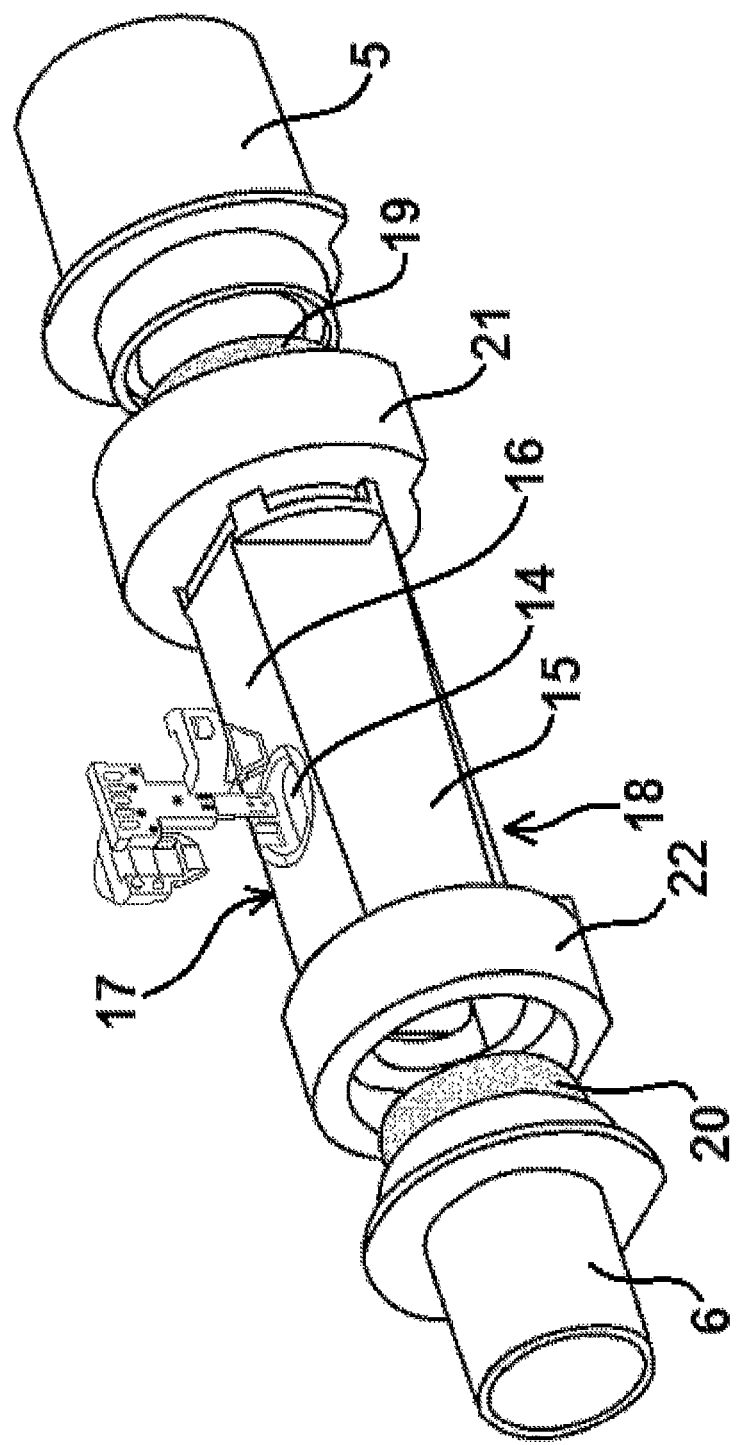
Figure 7:
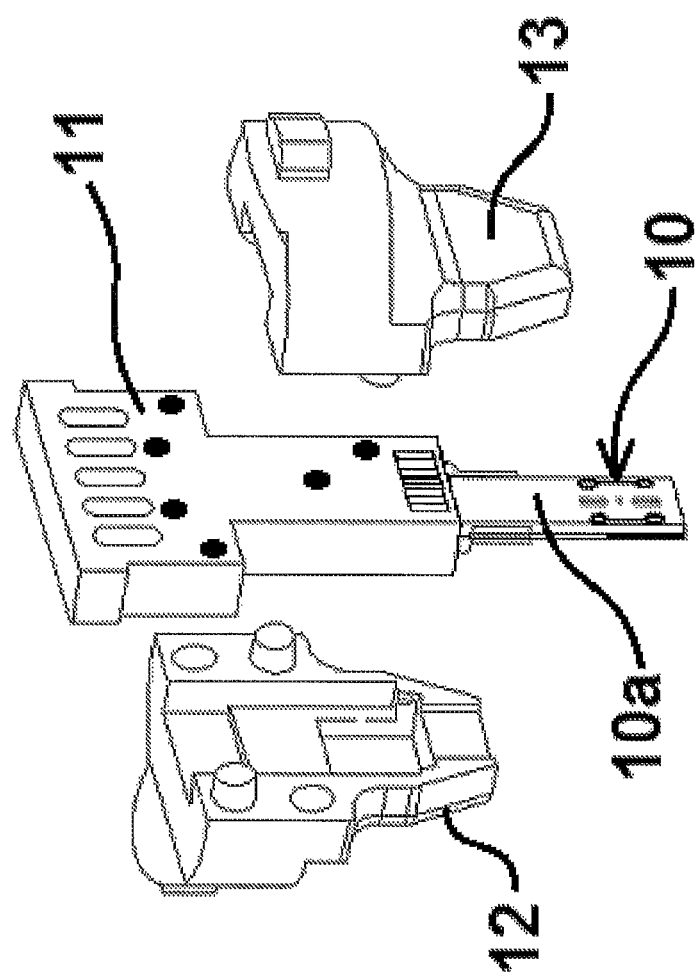
Figure 8:
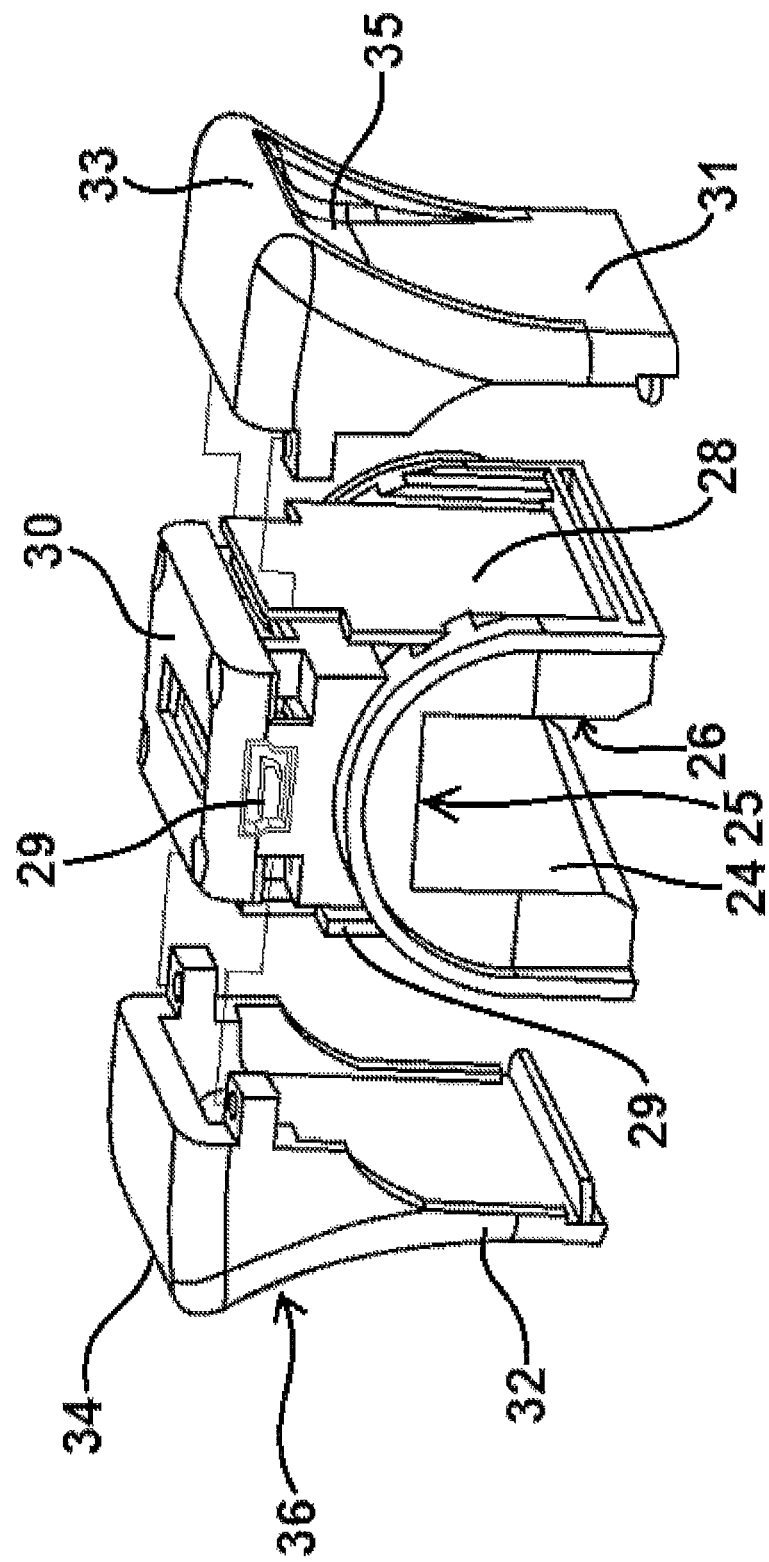

Model embodiments of the invention are represented in the drawing. Illustrations:

FIG. 1 First model embodiment of a device for artificial respiration in emergencies in a side view, FIG. 2 Device according to FIG. 1 separated into its individual components, FIG. 3 Flow tube with push-on part of the device according to FIG. 1 in a perspective view, FIG. 4 Flow tube with push-on part according to FIG. 3 in a view from below, FIG. 5 Flow tube according to FIG. 3 with push-on part lifted off, FIG. 6 Flow tube according to FIG. 3 in an exploded view, FIG. 7 Detail of FIG. 6 showing the sensor, the sensor circuit board and the sensor sleeves, FIG. 8 Push-on part according to FIG. 3, FIG. 9 Second model embodiment of a device for artificial respiration in emergencies in a front view, FIG. 10 Device according to FIG. 9 in a side view, FIG. 11 Flow tube and push-on part of the device according to FIG. 9 in a perspective view, FIG. 12 Flow tube of the device according to FIG. 9 in a perspective view, FIG. 13 Push-on part of the device according to FIG. 9 in a perspective view from above, FIG. 14 Push-on part of the device according to FIG. 9 in a perspective view from below, FIG. 15 Push-on part of the device according to FIG. 9 arranged on the arm of an aider.

DESCRIPTION OF THE MODEL EMBODIMENTS

FIGS. 1 to 8 show a first model embodiment of a device for artificial respiration in emergencies. The device exhibits a respiratory mask 40, a mouthpiece 41, a flow tube 2 and a push-on part 3. The respiratory mask is equipped with an elastic edge 42 so that it forms an airtight seal on the face of the casualty or person in an emergency situation. The respiratory mask 40 is usually pressed onto the face of a person with a degree of pressure so that no air can escape under the edge. To fasten the respiratory mask to a person, there are straps 43, 44 arranged on two sides of the respiratory mask. The two straps 43, 44 are placed around the head of a person and connected. As a result, the respiratory mask and, with it, the entire device, is secured to a person.

Figure 2:
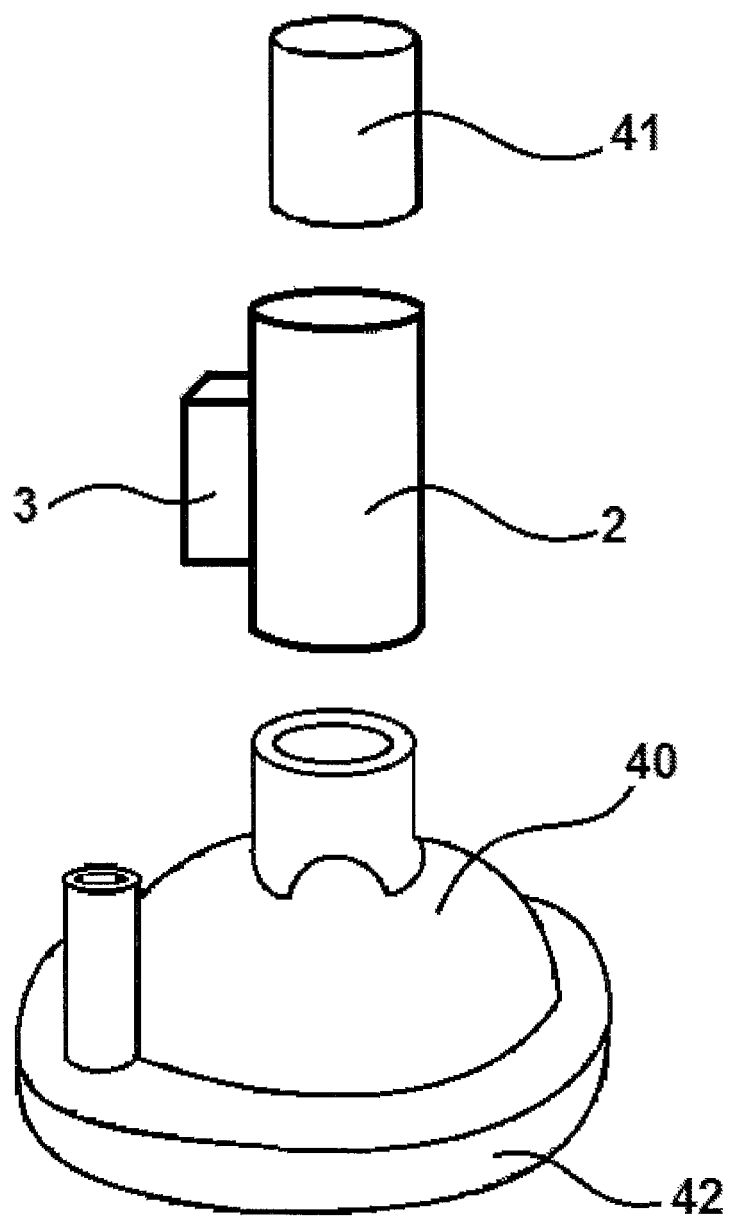
Figure 3:
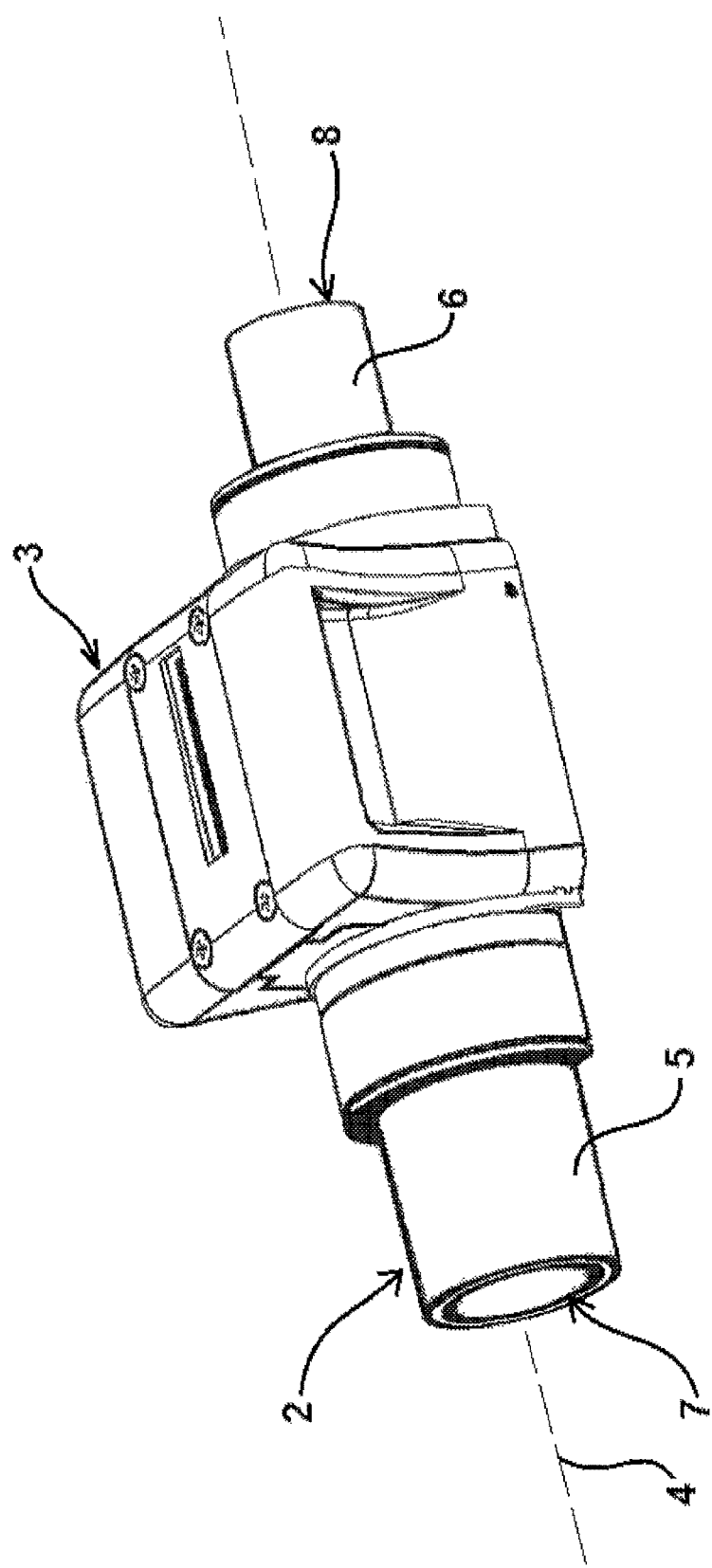
Figure 4:
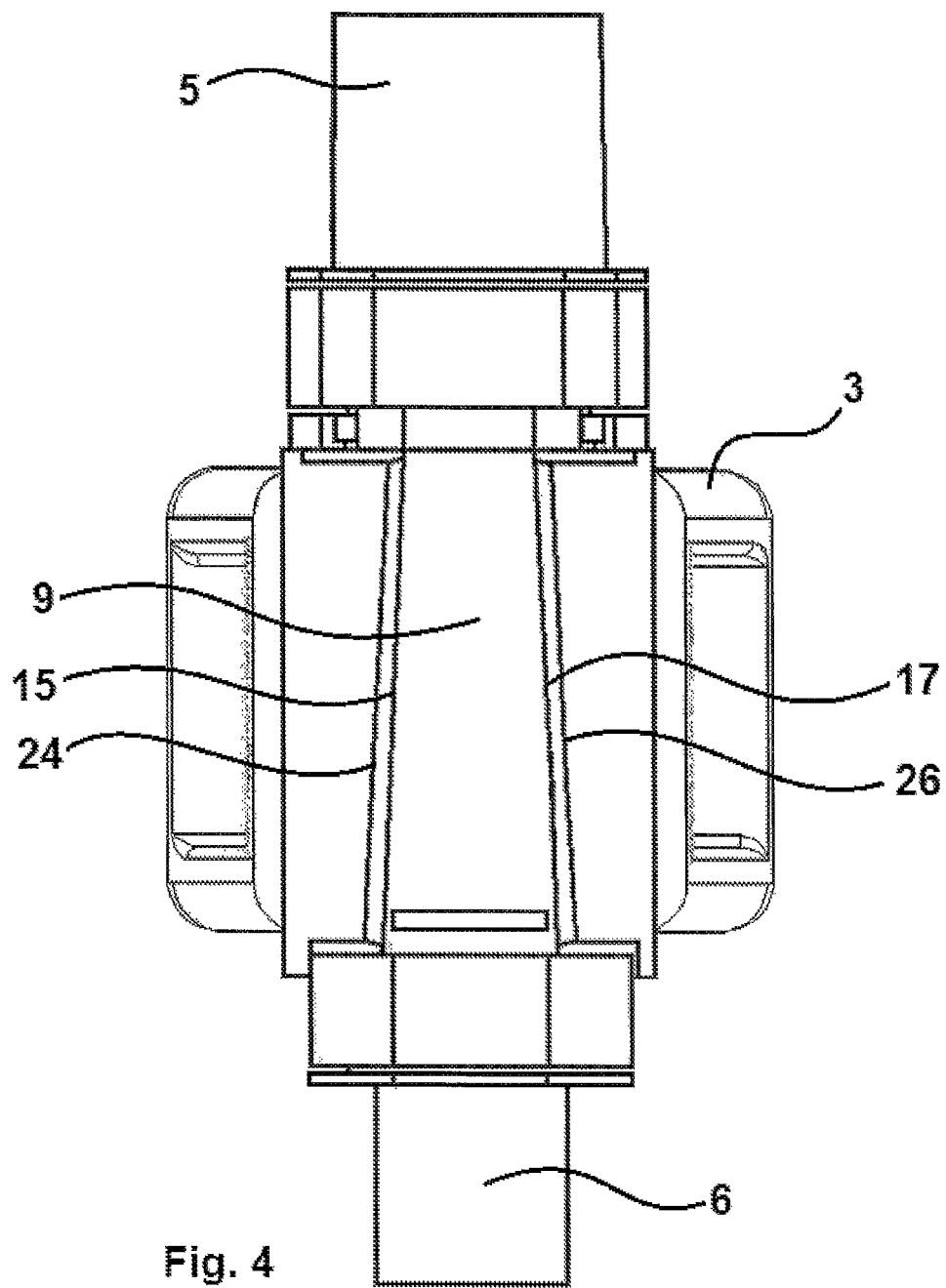

FIGS. 3 to 8 represent the flow tube 2 with the push-on part 3 shown in FIGS. 1 and 2. The flow tube is an elongate hollow body. Its longitudinal axis 4 corresponds to the direction of flow of the air flowing through the flow tube. On each of its ends the flow tube 2 exhibits one cylindrical end section 5, 6 with circular cross-sectional area. With these end sections 5, 6, one end of the flow tube 2 is introduced into the respiratory mask 40 and the other end into the mouthpiece 41. The flow tube 2 is open at the first face end 7 and at the second face end 8. Other than that, the flow tube is essentially closed. There is a sensor section 9 of the flow tube 2 between the end sections 5, 6 with the circular cross section. A flow sensor 10 is arranged on the sensor section 9. The attachment of the sensor 10 is discernible in FIG. 6. The flow sensor 10 is equipped with a sensor fixture device 10a and a sensor circuit board 11. As well as the flow sensor 10, further sensors can be arranged on the sensor fixture device 10a. The sensor circuit board 11 forms an extension of the sensor fixture device 10a. The sensor fixture device 10a can also be part of the sensor circuit board 11. The sensor circuit board 11 is held by two sensor sleeves 12 and 13. The sensor sleeves are adapted to a sensor opening 14 in the sensor section 9. The sensor circuit board 11 is pressed into the sensor opening 14 with the help of the sensor sleeves 12 and 13, thus locating the flow sensor. This clamps the sensor circuit board 11 between the two sensor sleeves 12, 13 and seals the sensor opening 14. The sensor now extends into the flow channel of the flow tube 2.

The sensor section 9 is limited by four side walls 15, 16, 17, 18. The two side walls 15 and 17 are flat and run at an angle of 5° to each other. The angle can also lie between 2° and 20°. The side wall 16 is likewise flat. It is adjacent to the two side walls 15 and 17. The fourth side wall 18 can likewise be flat or convex. If the fourth side wall 18 is flat in design, it is preferably parallel to the side wall 16. The four side walls 15, 16, 17, 18 produce the form of a truncated pyramid. The cross-section of the sensor section 9 is thus smaller at the end facing the cylindrical end section 5 of the flow tube 2 than at the end facing the cylindrical end section 6 of the flow tube 2. This is especially discernible in FIG. 2. Between the two ends, the cross-section decreases continuously perpendicular to the longitudinal axis of the flow tube 2. The cross-section increases continuously in the opposite direction.

A first filter 19 and a second filter 20 are discernible in FIG. 6. They are arranged on the ends of the two end sections 5, 6 of the flow tube 2 that face the sensor section 9. The sensor section 9 is equipped at its two ends with sleeves 21, 22 that encompass the cylindrical end sections 5, 6.

The push-on part 3 exhibits a housing 23. The housing 23 has a U-shape. It encompasses the sensor section 9 of the flow tube 2 from three sides so that the flat side walls 15, 16 and 17 are entirely covered by the push-on part. To that end, the push-on part exhibits three corresponding, flat side walls 24, 25 and 26 that rest on the side walls 15, 16 and 17. This is discernible in FIG. 4 with regard to the side walls 24 and 26 of the push-on part 3 and with regard to the side walls 15 and 17 of the sensor section 9. The two opposing side walls 24 and 26 of the push-on part 3 create a clamping force with which the push-on part 3 is connected to the flow tube 2 when it is pushed on.

In the housing 23 of the push-on part 3 there are circuit boards 27 and 28 on which electrical and electronic components are arranged. These are in particular a memory device and a processor. In addition an analog-to-digital converter and a DC voltage source can be arranged on the circuit boards. A connector socket not discernible in the drawing and into which the upper end of the circuit board 11 of the sensor 10 is inserted is arranged on the side wall 25. The connector socket is connected to the circuit boards 27, 28. It forms the interface to the sensor 10. In addition a connector socket 29 that forms an interface with an external reader—not represented in the drawing—is arranged on the front side of the housing 23. A display device can in addition be integrated into a cover 30 of the housing 23.

The two outer housing sections 31 and 32 cover the circuit boards 27, 28. They in addition exhibit handle elements 33, 34 that protrude outwards. These are equipped with grip recesses 35, 36 on their underside. The handle elements 33, 34 and the handle recesses 35, 36 facilitate pushing the push-on part 3 onto the flow tube 2 and lifting push-on part 3 off the flow tube 2.

To provide artificial respiration for a person in an emergency situation, the respiratory mask 40 is fitted over the nose and mouth of the person in an emergency situation and secured to the head of the person in an emergency situation with the straps 43, 44. The sensor is either already activated or is specifically activated. It determines the gases flowing through the flow tube 2. These gases are analyzed by the processor to obtain measured values. The processor matches the measured values up with a corresponding instruction that is stored in the storage device. This is displayed on the display device and emitted to the aider. The determination of the parameters for the gases flowing in the flow tube also continues during first aid. As a result, the instructions given to the aider during the course of first aid can be adapted continually to any changes in the condition of the person in an emergency situation.

FIGS. 9 to 15 show a second model embodiment of a device 101 for artificial respiration in emergencies. The device essentially corresponds to the first model embodiment with regard to the respiratory mask 40, mouthpiece 41 and flow tube 2. These components are therefore given the same reference numbers. The second model embodiment differs from the first model embodiment with regard to the push-on part 103. In a housing 123 of the push-on part 103 are arranged a processor not discernible in the drawing and an output device 124. They form an optical display device with several elongate light elements arranged parallel one above the other. The individual light elements exhibit light-emitting diodes in different colors. If only the bottom light element is switched on, no mass or volumetric flow is registered in the flow tube. If only the top light element is switched on, a maximum mass or volumetric flow is determined. The top and bottom light elements have different colors. The light elements between them have a third color. They indicate a mass or volumetric flow between the minimum and the maximum. The symbols on the left next to the light elements are arranged on buttons or pushbuttons. They are part of an input device 125. The symbols stand for adult, child or infant. By operating a button, the aider enters the group of people to which the person in a medical emergency situation belongs. The maximum and minimum of the mass or volumetric flow of the air flowing out of the person and the penetration depth for cardiac massage differ between these three groups of people.

Figure 9:
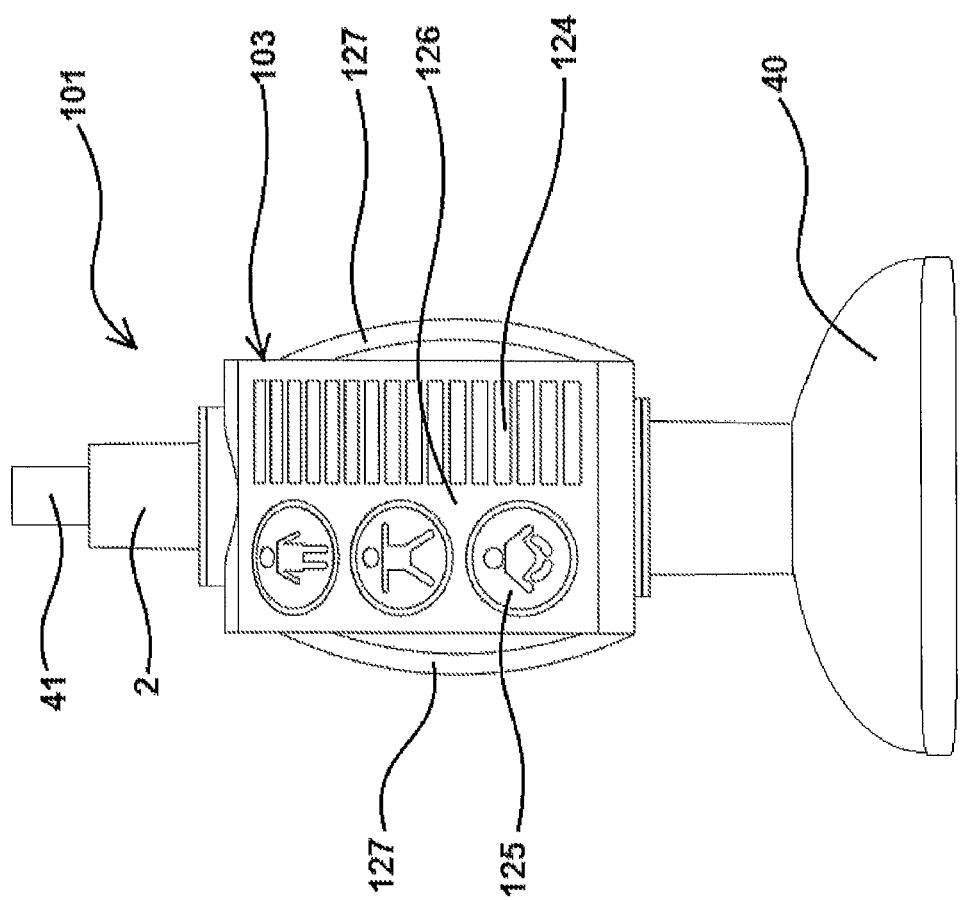
Figure 10:
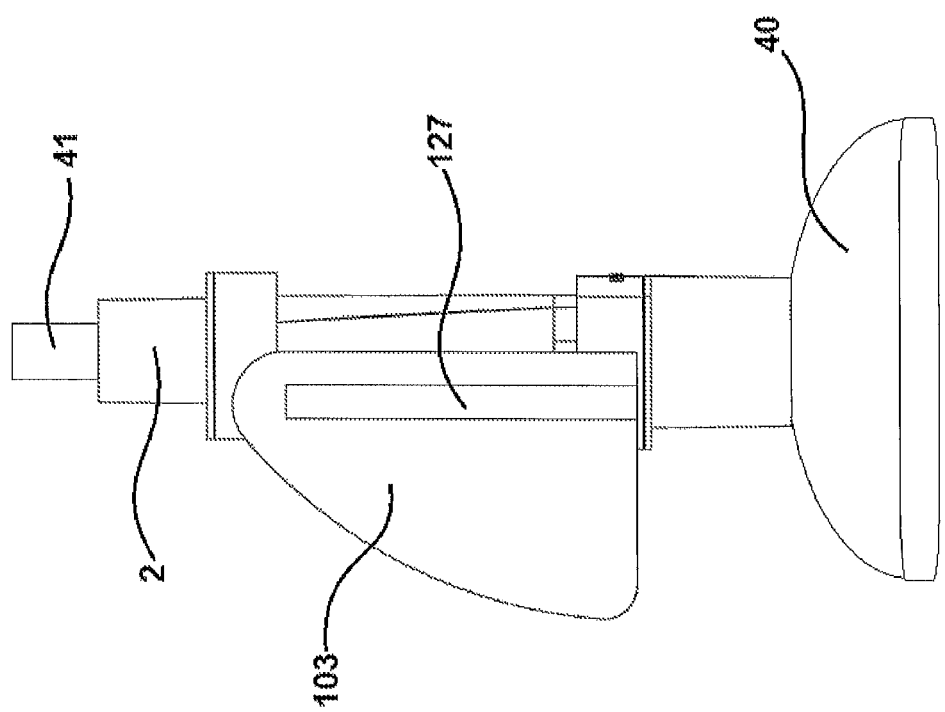

The surface of the push-on part 103 facing the viewer in FIG. 9 is an optically active surface 126. The light elements of the output device 124 are integrated into this surface 126. This surface is convex. This is discernible in the side view according to FIG. 10.

The push-on part 103 exhibits two handle elements 127 at the side on the housing 123. The push-on part 103 can be removed from the flow tube 2 with the help of these handle elements.

Figure 11:
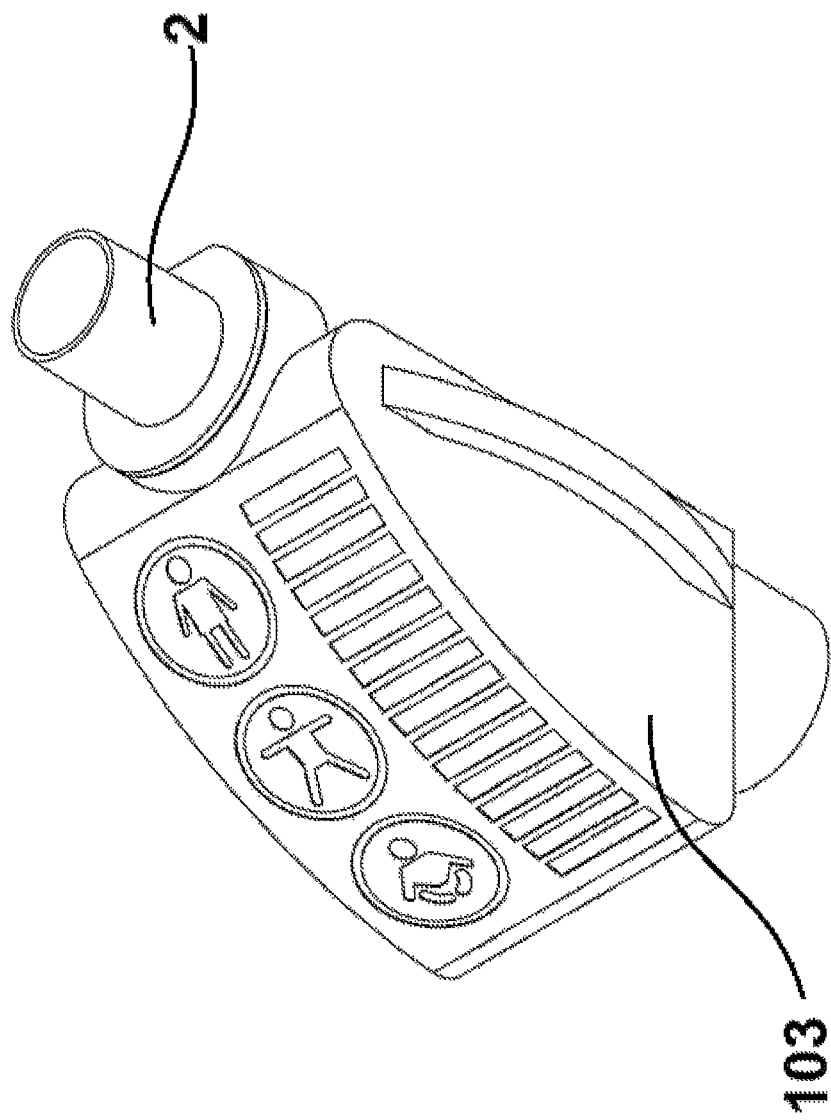

FIG. 11 shows the flow tube 2 and the push-on part 103 in a perspective view.

Figure 12:
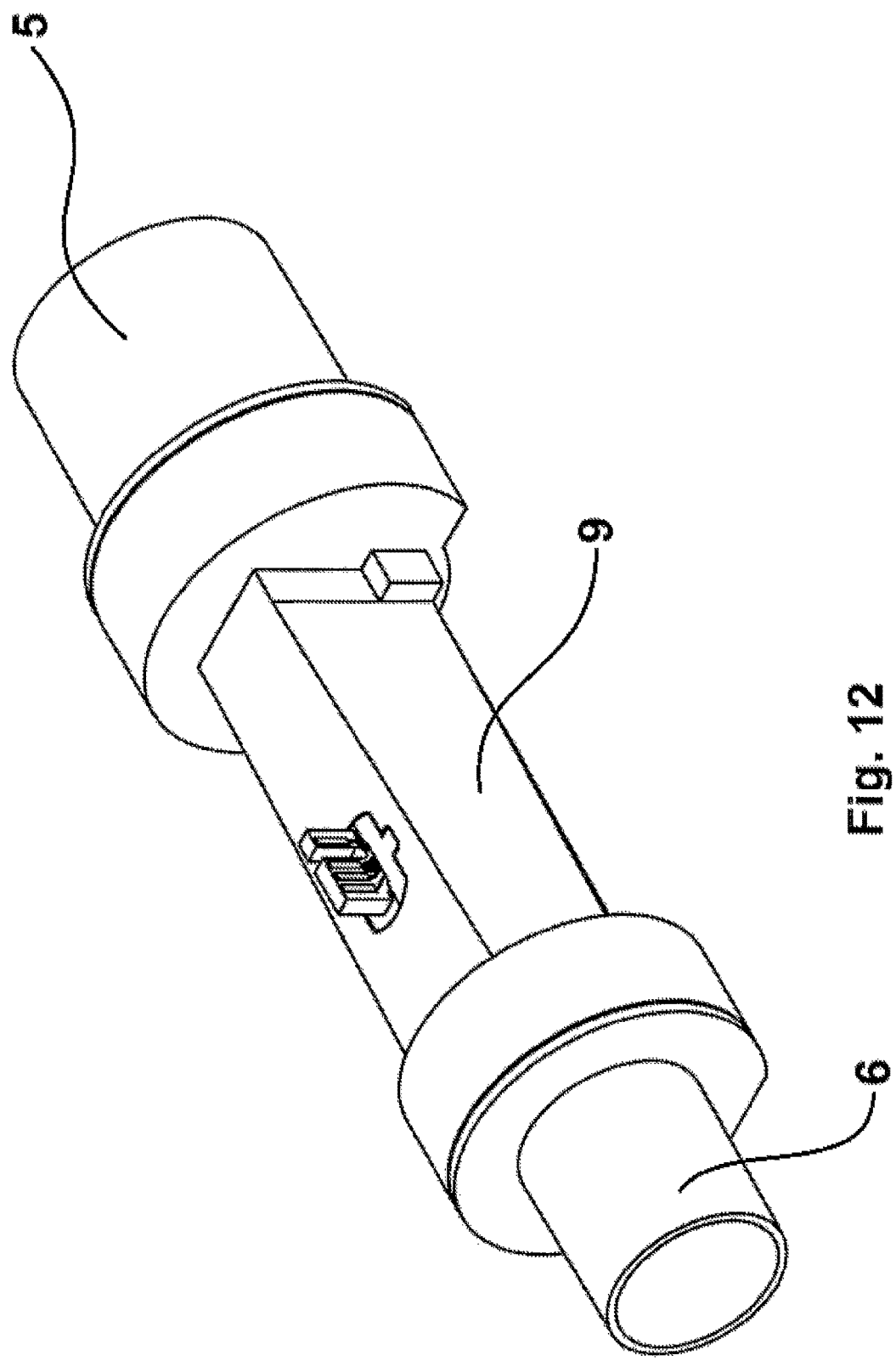

FIG. 12 shows the flow tube 2 with the two ends 5 and 6 and the sensor section 9. The description of the flow tube 2 of the first model embodiment otherwise applies.

Figure 13:
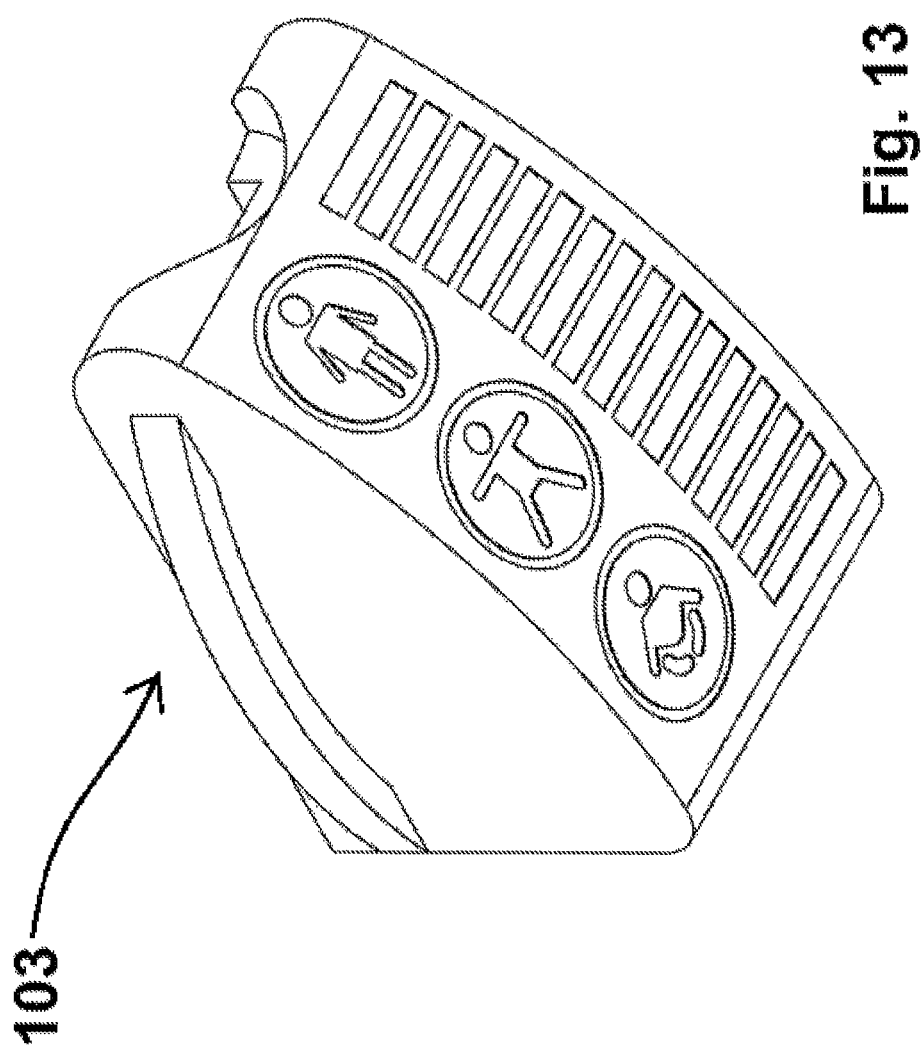

The push-on part 103 is represented in the FIGS. 13 and 14. The recess 128 in the housing 123 in which the flow tube 2 is inserted is discernible in FIG. 14.

FIG. 15 shows the push-on part 103 that is arranged on an arm 129 of an aider. To that end, the push-on part 103 is fastened to the arm with an arm fastening device 130 in the form of a strap. An acceleration sensor not discernible in the drawing is arranged in the push-on part 103.

To measure the mass or volumetric flow of a person, the device 103 with the respiratory mask 40 is placed onto the mouth and nose of the person. Using the input device 125, it is selected which group of people the person belongs to. The flow sensor in the flow tube determines the mass or volumetric flow of the air flowing out of the person. The mass or volumetric flow registered is displayed with the output device 124. If the mass or volumetric flow is too low, the aider administers a cardiac massage. If necessary the aider supplies air via the mouthpiece 41. In the cardiac massage, the mass or volumetric flow of the air flowing out of the person is determined. If no mass or volumetric flow is identified even though the penetration depth is increased, this is a sign of obstructed airways. In this case the aider can remove the push-on part 103 from the flow tube 2 and fasten it to their arm with the help of the arm fastening device 130. The penetration depth is now registered with the help of the acceleration sensor integrated into the housing 123. If the airways are not obstructed, the mass or volumetric flow of the air flowing out of the person can be continuously registered with every compression of the person's thorax and displayed on the display device. The mass or volumetric flow is a measure of the penetration depth in the cardiac massage. The aider learns from the display device whether the penetration depth was too low, sufficient or too high. They can modify the penetration depth accordingly in the next compression.

All features of the invention can be material to the invention both individually and in any combination.

REFERENCE NUMBERS

1 Device for artificial respiration in emergencies
2 Flow tube
3 Push-on part
4 Longitudinal axis
5 End of the flow tube
6 End of the flow tube
7 First face end of the flow tube
8 Second face end of the flow tube
9 Sensor section
10 Sensor
10a Sensor fixture device
11 Sensor circuit board
12 Sensor sleeve
13 Sensor sleeve
14 Sensor opening
15 Side wall
16 Side wall
17 Side wall
18 Side wall
19 First filter
20 Second filter
21 Sleeve
22 Sleeve
23 Housing 24 Side wall
25 Side wall
26 Side wall
27 Circuit board
28 Circuit board
29 Connector socket
30 Cover
31 Outer housing part
32 Outer housing part
33 Handle element
34 Handle element
35 Grip recess
36 Grip recess
40 Respiratory mask
41 Mouthpiece
42 Elastic edge
43 Strap
44 Strap
101 Device for artificial respiration in emergencies
103 Push-on part
123 Housing
124 Output device
125 Input device
126 Optically active surface
127 Handle element
128 Recess
129 Arm
130 Arm fastening device

The invention claimed is:

1. A device for artificial respiration of a person in a medical emergency situation, comprising
a respiratory mask which can be placed on the nose and mouth section of the person,
a mouthpiece, through which respiratory air can be supplied by an aider,
a flow tube disposed between the respiratory mask and the mouthpiece, which flow tube forms a continuous flow channel from the mouthpiece to the respiratory mask,
at least one flow sensor disposed in the flow channel of the flow tube, wherein the at least one flow sensor can determine a mass or volumetric flow of a gas flowing through the flow channel,
a processor designed to generate a characteristic penetration depth signal from the mass or volumetric flow registered by the at least one flow sensor for air flowing out of the nose and/or mouth of the person and through the flow channel during a cardiac massage as a result of a compression of the person's thorax down to a penetration depth,
an output device configured to emit the characteristic penetration depth signal, and
a push-on part configured to be connected detachably to the flow tube such that the push-on part encompasses the flow tube at least in part when connected to the flow tube, the processor and the output device being arranged in the push-on part;
wherein the push-on part is configured to be selectively attached to the flow tube and configured to be selectively fastened to an arm of the aider during cardiac massage; and
wherein the mass or volumetric flow is determined when the push-on part is selectively attached to the flow tube.

2. The device according to claim 1, further comprising a first vital signs sensor configured to register a proportion of oxygen and carbon dioxide in the air flowing through the flow channel, and
wherein the processor is designed to process the registered proportion of oxygen and carbon dioxide into a vital signs output signal, which is emitted by the output device.

3. The device according to claim 2, further comprising a second vital signs sensor that registers a pressure difference in the flow channel as a vital sign of the person.

4. The device according to claim 1, wherein the output device comprises an optical display device.

5. The device according to claim 4, wherein the optical display device comprises an optically active surface on which the output signal is displayed, and
wherein the optically active surface is a convex surface or essentially a flat surface, and wherein the flat optically active surface includes an angle of more than 0° and less than 90° with a longitudinal direction of the flow tube, where the longitudinal direction essentially corresponds to a direction of flow of the gas flowing through the flow channel.

6. The device according to claim 4, wherein the optical display device comprises several light-emitting diodes (LEDs).

7. The device according to claim 1, wherein the output device has an acoustic output device.

8. The device according to claim 1, further comprising an interface,
wherein a mass or volumetric flow value registered by the at least one flow sensor or data derived therefrom can be emitted over the interface to an external device for emergency care, to a medical device, to a computer and/or to a mobile telecommunications device.

9. The device according to claim 1, wherein a filter is arranged in the flow channel between the mouthpiece and the at least one flow sensor and/or a filter is arranged in the flow channel between the respiratory mask and the at least one flow sensor.

10. The device according to claim 1, wherein the output device is designed to indicate whether the mass or volumetric flow registered or the characteristic penetration depth signal derived from the mass or volumetric flow or another parameter derived from the mass or volumetric flow lies within a specified range for resuscitation.

11. The device according to claim 1, wherein the push-on part comprises an arm fastening device configured to fasten the device to the arm of the aider, and
wherein the push-on part comprises an acceleration sensor-configured to register an acceleration of the arm during a cardiac massage when the push-on part is fastened to the arm of the aider.

12. The device according to claim 11, wherein the processor is designed to generate an acceleration output signal from the acceleration registered by the acceleration signal, which acceleration output signal can be emitted by the output device.

13. A method for artificial respiration of a person in a medical emergency situation, using a device comprising
a respiratory mask,
a mouthpiece,
a flow tube connecting the mouthpiece with the respiratory mask,
a flow sensor arranged on the flow tube,
a processor,
an output device, and
a push-on part connected detachably to the flow tube such that the push-on part encompasses the flow tube at least in part, the processor and the output device being arranged in the push-on part, wherein the push-on part is configured to be selectively attached to the flow tube and configured to be selectively fastened to an arm of an aider during cardiac massage;

the method comprising process steps of:
fitting the respiratory mask onto the nose and mouth section of the person,
starting a cardiac massage of the person via compressing a thorax of the person down to a penetration depth and then allowing the thorax to decompress,
registering, via the flow sensor, a mass or volumetric flow of a gas flowing out of the nose and/or mouth and flowing through the flow tube as a result of the cardiac massage while the push-on part is selectively attached to the flow tube,
processing, via the processor, the mass or volumetric flow registered by the flow sensor to obtain a characteristic penetration depth signal for the penetration depth, and
emitting, via the output device, the characteristic penetration depth signal.

14. The method according to claim 13, further comprising:
registering, via an additional sensor, a proportion of oxygen and carbon dioxide in the gas flowing through the flow tube,
processing, via the processor, the proportion of oxygen and carbon dioxide registered into a vital signs output signal, and
emitting, via the output device, the vital signs output signal.

15. The method according to claim 13, further comprising:
indicating, via the output device, whether the mass or volumetric flow registered or the characteristic penetration depth signal derived from the mass or volumetric flow or another parameter derived from the mass or volumetric flow lies within a specified range for resuscitation.

16. The method according to claim 13, further comprising:
registering, via the flow sensor, an initial mass or volumetric flow of air flowing out of the nose and/or mouth of the person before the cardiac massage starts, and
emitting, via the output device, whether the initial mass or volumetric flow registered is within a specified range for spontaneous breathing.

17. The method according to claim 13, further comprising:
detaching the push-on part from the flow tube such that the push-on part no longer surrounds the flow tube,
fastening the push-on part to the arm of the aider,
registering, via an acceleration sensor of the push-on part, an acceleration with which the thorax is compressed during the compression of the thorax when the push-on part is fastened to the arm of the aider,
determining a further characteristic penetration depth signal for the penetration depth from the acceleration determined,
emitting, via the output device, the further characteristic penetration depth signal, and
indicating, via the output device, whether the acceleration registered or the further characteristic penetration depth signal derived from the acceleration or another parameter derived from the acceleration lies within a specified range for resuscitation.

18. The method according to claim 17, wherein the push-on part is fastened to the wrist of the aider.

* * * * *